United States Patent
Tass et al.

(10) Patent No.: US 11,013,918 B2
(45) Date of Patent: May 25, 2021

(54) DEVICE AND METHOD FOR EFFECTIVE, INVASIVE, AND AMPLITUDE-MODULATED NEUROSTIMULATION

(71) Applicant: Forschungszentrum Juelich GmbH, Juelich (DE)

(72) Inventors: Peter Alexander Tass, Tegernsee (DE); Oleksandr Popovych, Dueren (DE)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 222 days.

(21) Appl. No.: 16/084,751

(22) PCT Filed: Mar. 14, 2017

(86) PCT No.: PCT/EP2017/055915
§ 371 (c)(1),
(2) Date: Sep. 13, 2018

(87) PCT Pub. No.: WO2017/157890
PCT Pub. Date: Sep. 21, 2017

(65) Prior Publication Data
US 2019/0083785 A1    Mar. 21, 2019

(30) Foreign Application Priority Data
Mar. 16, 2016 (DE) .......................... 102016104913.1

(51) Int. Cl.
*A61N 1/36* (2006.01)
*A61N 5/06* (2006.01)
(Continued)

(52) U.S. Cl.
CPC ............ *A61N 1/36062* (2017.08); *A61B 5/24* (2021.01); *A61B 5/4836* (2013.01);
(Continued)

(58) Field of Classification Search
CPC .......................... A61N 1/36062; A61N 1/3605
See application file for complete search history.

(56) References Cited

U.S. PATENT DOCUMENTS 7,974,698 B2 *   7/2011   Tass ................... A61N 1/36135
                                              607/45
8,543,219 B2 *   9/2013   Tass ..................... A61M 21/00
                                              607/72
(Continued)

OTHER PUBLICATIONS

PCT/EP2017/055915 International Search Report dated May 9, 2017.

*Primary Examiner* — John R Downey
(74) *Attorney, Agent, or Firm* — Leydig, Voit & Mayer, Ltd.

(57) ABSTRACT

A device and method is provided for stimulation of neurons. The device includes a stimulation unit that can be implanted into a body of a patient and has stimulation elements that apply a stimulation signal to tissue of the patient to stimulate neurons in the brain and/or the spinal cord of the patient. Moreover, a measuring unit receive a measurement signal that reflects a neuronal activity of the stimulated neurons. Further, a control unit generate a modulation signal from the measurement signal, and modulates an amplitude of a pulse train with the modulation signal. Individual pulses of the pulse train include a first and second pulse portions that introduce and remove charge from the tissue. Moreover, the control unit varies a pause between the pulse portions until the synchronization of the stimulated neurons is minimized or falls below a predetermined threshold.

20 Claims, 6 Drawing Sheets

(51) Int. Cl.
  *A61B 5/00* (2006.01)
  *A61B 5/24* (2021.01)
  *A61N 5/067* (2006.01)
  *A61B 5/16* (2006.01)
  *A61B 5/245* (2021.01)
  *A61B 5/291* (2021.01)
  *A61B 5/296* (2021.01)

(52) U.S. Cl.
  CPC ....... *A61N 1/3605* (2013.01); *A61N 1/36075* (2013.01); *A61N 1/36171* (2013.01); *A61N 1/36178* (2013.01); *A61N 1/36189* (2013.01); *A61N 5/0601* (2013.01); *A61N 5/0622* (2013.01); *A61B 5/165* (2013.01); *A61B 5/245* (2021.01); *A61B 5/291* (2021.01); *A61B 5/296* (2021.01); *A61B 5/4035* (2013.01); *A61B 5/4082* (2013.01); *A61B 5/4088* (2013.01); *A61B 5/4094* (2013.01); *A61B 5/7253* (2013.01); *A61B 2562/0219* (2013.01); *A61N 1/36064* (2013.01); *A61N 1/36067* (2013.01); *A61N 1/36071* (2013.01); *A61N 1/36082* (2013.01); *A61N 1/36103* (2013.01); *A61N 1/36135* (2013.01); *A61N 1/36192* (2013.01); *A61N 2005/067* (2013.01); *A61N 2005/0612* (2013.01); *A61N 2005/0651* (2013.01)

(56) References Cited

U.S. PATENT DOCUMENTS

| | | | |
|---|---|---|---|
| 2006/0212089 A1* | 9/2006 | Tass | A61N 1/36082 607/45 |
| 2007/0203532 A1* | 8/2007 | Tass | A61N 1/36146 607/45 |
| 2008/0046025 A1* | 2/2008 | Tass | A61N 1/0551 607/45 |
| 2008/0058892 A1* | 3/2008 | Haefner | A61N 1/36053 607/45 |
| 2010/0121399 A1* | 5/2010 | McCabe | A61N 1/36128 607/17 |
| 2010/0217355 A1* | 8/2010 | Tass | A61N 1/0551 607/62 |
| 2011/0009921 A1* | 1/2011 | Tass | A61H 23/00 607/45 |
| 2011/0201977 A1 | 8/2011 | Tess et al. | |
| 2013/0090519 A1 | 4/2013 | Tass et al. | |
| 2014/0135858 A1* | 5/2014 | Ahmed | A61N 1/36082 607/3 |
| 2014/0336547 A1 | 11/2014 | Tass et al. | |

* cited by examiner

DEVICE AND METHOD FOR EFFECTIVE, INVASIVE, AND AMPLITUDE-MODULATED NEUROSTIMULATION

CROSS REFERENCE TO RELATED APPLICATIONS

This application is a 35 U.S.C. § 371 National Phase of PCT Application No. PCT/EP2017/055915 filed Mar. 14, 2017, which claims benefit to DE Application No. 10 2016 104913.1 filed Mar. 16, 2016, the disclosure of each of which is hereby incorporated by reference in their entirety.

TECHNICAL FIELD

The invention relates to a device and a method for effective, invasive, and amplitude-modulated neurostimulation.

BACKGROUND

In patients with neurological or psychiatric illnesses, e.g., Parkinson's disease, essential tremor, dystonia, or obsessive-compulsive disorders, nerve cell assemblies in circumscribed regions of the brain, e.g., of the thalamus and the basal ganglia, are pathologically, e.g., excessively synchronously, active. In this case, a large number of neurons synchronously forms action potentials, i.e., the neurons involved fire excessively synchronously. In healthy persons, on the other hand, the neurons in these brain sectors fire qualitatively differently, e.g., in an uncorrelated manner.

In Parkinson's disease, the pathologically synchronous activity changes the neuronal activity in other brain sectors, e.g., in areas of the cerebral cortex such as the primary motor cortex. In this respect, the pathologically synchronous activity in the region of the thalamus and of the basal ganglia, for example, imposes its rhythm on the cerebral cortex areas such that, ultimately, the muscles controlled by these areas develop pathological activity, e.g., a rhythmic trembling (tremor).

Deep brain stimulation is used to treat Parkinson's patients who cannot be sufficiently treated by medication. In this case, deep electrodes are implanted in specific brain sectors, e.g., in the subthalamic nucleus. An electrical stimulation is carried out via the deep electrodes to relieve the symptoms. With the standard high-frequency stimulation for treating Parkinson's disease, a so-called high-frequency permanent stimulation is carried out at frequencies of more than 100 Hz. This kind of treatment has no long-lasting therapeutic effects (cf. P. Temperli, J. Ghika, J.-G. Villemure, P. Burkhard, J. Bogousslaysky, and F. Vingerhoets: How do Parkinsonian signs return after discontinuation of subthalamic DBS? Neurology 60, 78 (2003)). Long-lasting therapeutic effects may be produced via "coordinated reset" stimulation (CR stimulation), and moreover with markedly less stimulation (e.g. stimulation current) (cf. P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012); I. Adamchic, C. Hauptmann, U. B. Barnikol, N. Pawelcyk, O. V. Popovych, T. Barnikol, A. Silchenko, J. Volkmann, G. Deuschl, W. Meissner, M. Maarouf, V. Sturm, H.-J. Freund, P. A. Tass: Coordinated Reset Has Lasting Aftereffects in Patients with Parkinson's Disease. Movement Disorders 29, 1679 (2014)).

With other diseases, e.g., epilepsy, that cannot be sufficiently treated with medication, different electrodes, e.g., epicortical or epidural electrodes, are also implanted in addition to deep electrodes. With further diseases, e.g., chronic pain syndromes, it is customary to stimulate the spinal cord not only by means of deep electrodes in the brain, but also by means of epidural electrodes, for example. In contrast to CR stimulation, most other types of stimulation have no long-lasting therapeutic effects.

Therapeutic effects can also be achieved by direct stimulation of the brain tissue or spinal cord by light, e.g., via implanted light guides. Different spatiotemporal stimulation patterns, such as CR stimulation, can also be used in this respect.

The effect of the CR stimulation may be markedly reduced, or even prevented, by a disadvantageous selection of the stimulation parameters, in particular of the CR stimulation frequency and the stimulation intensity in the sense of the amplitude of the individual stimuli and/or the duration of the individual stimuli. Incorrectly or sub-optimally selected parameters may weaken or even completely suppress the stimulation success. It is thus important to calibrate the stimulation parameters. Since parameters of the stimulated tissue are subjected to chronological fluctuations, a calibration taking place at sufficient time intervals is necessary. Since such fluctuations may occur in an unpredictable manner, the calibration is to be performed comparatively often in an "open loop" mode, and/or feedback signals are to be derived in a "closed loop" mode, which feedback signals may indicate the necessity of re-calibration, for example in the sense of exceeding a tolerable neuronal synchronisation.

For this reason, stimulation methods have been developed which make do with markedly fewer stimulation parameters than CR stimulation, for example linear delayed feedback stimulation (cf. M. G. Rosenblum, A. S. Pikovsky: Controlling synchronization in an ensemble of globally coupled oscillators. Physical Review Letters 92, 114102 (2004)), or non-linear delayed feedback stimulation (cf. O. V. Popovych, C. Hauptmann, P. A. Tass: Effective Desynchronization by Nonlinear Delayed Feedback. Physical Review Letters 94, 164102 (2005)), respectively via one or more stimulation contacts. Conventional non-linear delayed feedback stimulation is clearly superior to conventional linear delayed feedback stimulation in that in the former a desynchronization may be achieved over wide ranges of the time delay, whereas in the latter a desynchronization may be achieved only in narrow ranges of the time delay; outside of these narrow ranges, this stimulation method leads to a synchronization or stabilizes the synchronous state.

Both conventional linear delayed feedback stimulation and conventional non-linear delayed feedback stimulation are very limited in their effectiveness, since at therapeutically effective stimulation strengths, the charge introduction per half-oscillation typically markedly exceeds the allowable upper limits for avoiding tissue damage (cf. S. B. Brummer, M. Turner, M.: Electrical stimulation of the nervous system: the principle of safe charge injection with noble metal electrodes. Bioelectrochem. Bioenerg. 2, 13 (1975); S. B. Brummer, L. S. Robblee, F. T. Hambrecht: Criteria for selecting electrodes for electrical stimulation: theoretical and practical considerations. Ann. N. Y. Acad. Sci. 405. 159 (1983); D. Harnack, C. Winter, W. Meissner, T. Reum, A. Kupsch, R. Morgenstern: The effects of electrode material, charge density and stimulation duration on the safety of high-frequency stimulation of the subthalamic nucleus in rats. J. Neurosci. Methods 138, 207 (2004)). This is due to the fact that linear delayed feedback stimulation uses as a stimulation signal the measured signal of the neuron population to be desynchronized or an oscillatory signal connected sufficiently closely coupled thereto after amplification, bandpass filtering (or analogous pre-processing to extract the relevant pathological frequency component), and time delay (typically with half of the mean period of the synchronized oscillation). Due to the low stimulation frequency resulting therefrom, the charge introduction already exceeds the allowable upper limits at comparatively low stimulus strengths. In non-linear delayed feedback stimulation, a stimulation signal with the same dominant frequency as in linear delayed feedback stimulation is generated in the same manner by non-linearly offsetting the delayed and non-delayed pre-processed signals.

SUMMARY OF THE INVENTION

The invention is based on the aim of specifying a device and a method for the stimulation of neurons, with which device and method the stimulation can be performed in a markedly less error-prone and more robust manner in comparison to the prior art, and the desired desynchronization effect can be achieved without complicated calibration.

The aim underlying the invention is achieved by the features of the independent claims. Advantageous developments and embodiments of the invention are specified in the dependent claims.

BRIEF DESCRIPTION OF THE DRAWINGS

The invention is explained in more detail below by way of example with reference to the drawings. Shown are.

DETAILED DESCRIPTION

Figure 1:
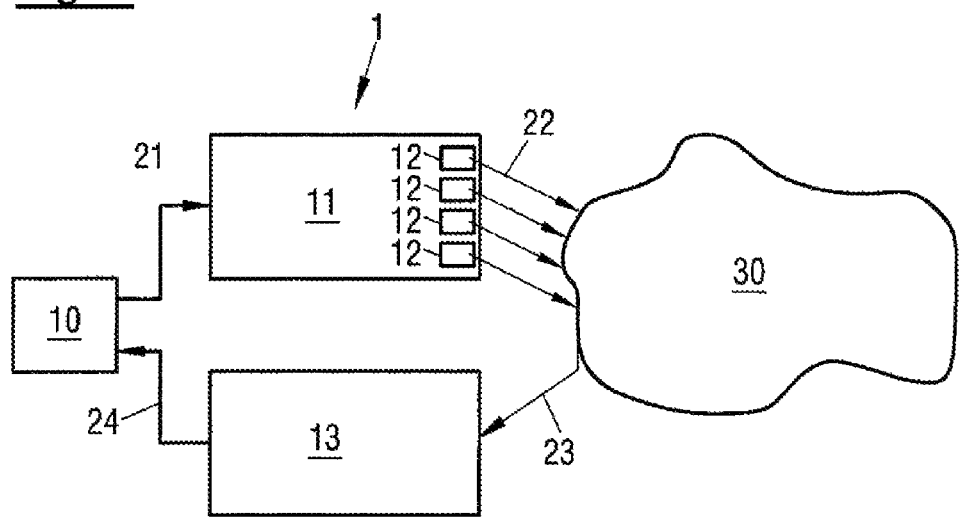
FIG. 1 illustrates a schematic illustration of a device for desynchronization of neurons with pathologically synchronous and oscillatory neuronal activity, according to one embodiment.

FIG. 1 schematically shows a device 1 for stimulating neurons having a pathologically synchronous and oscillatory neuronal activity. The device 1 is comprised of a control unit 10, a stimulation unit 11 having one or more stimulation elements 12, and a measuring unit 13.

In the embodiment illustrated in FIG. 1, the stimulation unit 11 contains four stimulation elements 12, for example. The stimulation unit 11 can naturally, however, also have a different number of stimulation elements 12. In the case of electrical stimulation, the stimulation elements 12 may, for example, be stimulation contact surfaces of one or more electrodes for applying electrical stimuli to the neuronal tissue. If stimulation takes place optically, light guides can, for example, be used as stimulation elements 12 in order to stimulate the neuronal tissue with light stimuli at the desired points.

The control unit 10 is coupled with the stimulation unit 11 and the measuring unit 13, and implements a control of the stimulation unit 11 during operation of the device 1. To this end, the control unit 10 generates control signals 21, which are received by the stimulation unit 11.

The stimulation unit 11 is surgically implanted into the body of the patient and generates, on the basis of the control signals 21, one or more stimulation signals or stimuli 22—in particular, electrical and/or optical stimulation signals 22—which are applied to the tissue of the patient in order to thus stimulate neurons in a target area 30 in the brain and/or spinal cord of the patient. The stimulation signals 22 are in particular designed to desynchronize the neurons having the pathologically synchronous and oscillatory activity upon administration to the patient.

The measuring unit 13 receives one or more measurement signals 23 measured on the patient, converts them into electrical signals 24 where applicable, and transmits them to the control unit 10. The neuronal activity in the stimulated target area 30 or in a sector connected to the target area 30 can, in particular, be measured by means of the measuring unit 13, wherein the neuronal activity of this sector sufficiently closely correlates with the neuronal activity of the target sector 30. A non-neuronal, e.g., muscular, activity, or the activation of the autonomous nervous system, may also be measured by means of the measuring unit 13 insofar as this activity or activation is sufficiently closely correlated with the neuronal activity of the target area 30. The stimulation effect achieved by the stimulation signals 22 may furthermore be monitored with the aid of the measuring unit 13.

The measuring unit 13 contains one or more sensors that, in particular, enable the amplitude of the pathological oscillatory neuronal activity to be recorded.

The sensors can be implanted into the body of the patient. For example, epicortical electrodes, deep brain electrodes for measuring, for example, local field potentials, subdural or epidural brain electrodes, subcutaneous EEG electrodes, and subdural or epidural spinal cord electrodes can serve as invasive sensors. The deep electrodes for measuring the local field potentials may also be structurally combined with, or even be identical to, the electrodes used for stimulation. The contacts of the electrodes may be placed such that they can derive relevant neuronal feedback signals.

Alternatively, non-invasive sensors can be used, e.g., chronically or intermittently used electroencephalography (EEG) or electromyography (EMG) electrodes, or magnetoencephalography (MEG) sensors. The neuronal activity can also be determined by detecting characteristic movement patterns, such as tremor, akinesia, or epileptic seizures, with the aid of an accelerometer or gyroscope, or indirectly by measuring activation of the autonomous nervous system using the measurement of skin resistance. In the case of LFP, EEG and/or MEG signals, the underlying currents may be calculated by means of inverse methods known to the person skilled in the art and be used as the feedback modulation signals described further below.

The control unit 10 processes the signals 24; e.g., the signals 24 may be amplified and/or filtered. The control unit 10 also generates from the signals 24, and therefore from the measurement signal 23, a modulation signal with which the amplitude of a pulse train comprising a plurality of individual pulses is modulated. The control unit 10 controls the stimulation unit 11 such that the at least one stimulation element 12 administers the amplitude-modulated pulse train to the tissue as the stimulation signal 22 in order to therewith stimulate the neurons in the target area 30. The individual pulses of the pulse train are respectively comprised of a first pulse portion and a second pulse portion following the first pulse portion. One of the first pulse portion and second pulse portion introduces charge into the tissue, and the other pulse portion removes charge from the tissue. A pause is also respectively observed between the first pulse portion and the second pulse portion of the individual pulses.

The control unit 10 can be a non-invasive unit, i.e., it is outside the body of the patient during operation of the device 1 and is not surgically implanted into the body of the patient.

The individual components of the device 1—in particular the control unit 10, the stimulation unit 11, and/or the measuring unit 13—may be structurally separate from one another. The device 1 may therefore also be construed as a system. To implement its tasks, the control unit 10 may contain a processor—for example, a microcontroller. The stimulation methods described here may be stored as software code in a memory associated with the control unit 10.

The device 1 may, in particular, be used to treat neurological or psychiatric diseases, e.g., Parkinson's disease, essential tremor, tremor resulting from multiple sclerosis as well as other pathological tremors, dystonia, epilepsy, depression, locomotor disorders, cerebellar diseases, obsessive-compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension, as well as other diseases that are characterized by pathologically increased neuronal synchronisation.

The aforementioned diseases can be caused by a disorder of the bioelectrical communication of neuronal assemblies that are connected in specific circuits. In this respect, a neuronal population continuously generates pathological neuronal activity and possibly a pathological connectivity (network structure) associated therewith. In this respect, a large number of neurons synchronously forms action potentials, i.e., the neurons involved fire excessively synchronously. In addition, the pathological neuronal population has an oscillatory neuronal activity, i.e., the neurons fire rhythmically. In the case of neurological or psychiatric diseases, the mean frequency of the pathological rhythmic activity of the affected neuronal assemblies lies approximately in the range of 1 to 30 Hz but can also be outside this range. In healthy people, on the other hand, the neurons fire qualitatively differently, e.g., in an uncorrelated manner.

Figure 2:
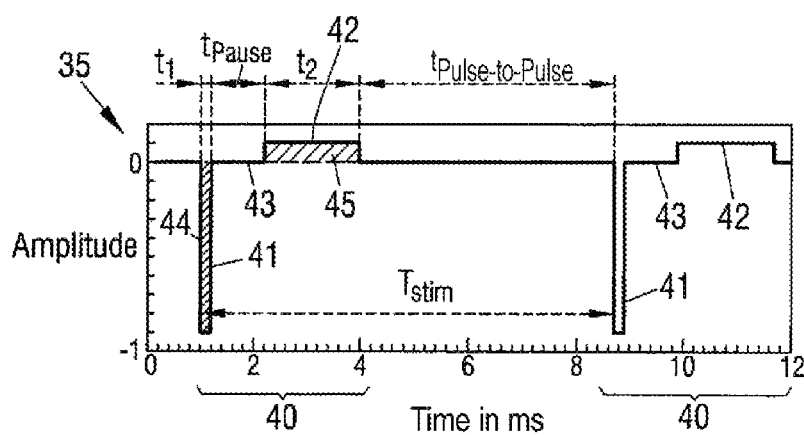
FIG. 2 illustrates a schematic illustration of a pulse train with individual pulses that have a pause between a first pulse portion and a second pulse portion following the first pulse portion.

In FIG. 2, a section of a pulse train 35 is shown by way of example, from which pulse train 35 a stimulation signal or stimulus 22 for stimulation of the neurons in the target area 30 may be generated. FIG. 2 shows the pulse train 35 before implementation of the amplitude modulation.

The pulse train 35 is comprised of a plurality of individual pulses 40 that in particular repeat periodically, and of which two individual pulses 40 are shown by way of example in FIG. 2. In FIG. 2, the amplitude or the signal strength of the individual pulses 40 is plotted, for example in normalized units, against the time in ms.

Each of the individual pulses 40 is comprised of a first pulse portion 41, a second pulse portion 42 following the first pulse portion 41, and a pause 43 situated between the first pulse portion 41 and the second pulse portion 42. The first pulse portion 41 has a duration $t_1$, the second pulse portion 42 has a duration $t_2$, and the pause has a duration $t_{Pause}$.

The first and second pulse portion 41, 42 are designed such that one of the two pulse portions 41, 42 introduces charge into the tissue, and the other pulse portion removes charge from the tissue. In the embodiment illustrated in FIG. 2, the first pulse portion 41 introduces charge into the tissue, and the second pulse portion 42 removes charge from the tissue. Alternatively, it may be provided that the first pulse portion 41 removes charge from the tissue, and the second pulse portion 42 provides charge to the tissue.

The magnitude of the amplitude of the first pulse portion 41 is greater than the magnitude of the amplitude of the second pulse portion 42. On the other hand, the duration $t_2$ of the second pulse portion 42 is longer than the duration $t_1$ of the first pulse portion 41. The two pulse portions 41, 42 are ideally dimensioned such that the charge that is transferred by them is of the same magnitude in both pulse portions 41, 42, meaning that the areas 44 and 45 that are shaded in the drawing in FIG. 2 and that are obtained via integration of the pulse portions 41 or 42 over time, are of the same size. As a result, just as much charge is introduced into the tissue by an individual pulse 40 during the actual stimulation phase of duration $t_1$ as is removed from the tissue during the charge-balancing stimulation phase of duration $t_2$. Such pulses are called charge-balanced pulses.

The duration $t_1$ of the first pulse portion 41 is in particular in a range between 1 μs and 450 μs. Insofar as this concerns an electrical stimulation, the individual pulses 40 may be current-controlled or voltage-controlled pulses. In the case of current-controlled pulses, the amplitude of the first pulse portion 41 may be up to 25 mA, and in the case of voltage-controlled pulses, the amplitude of the first pulse portion 41 may be up to 16 V.

During the pause 43 situated between the first pulse portion 41 and the second pulse portion 42, the amplitude of the individual pulse 40 is equal to zero, meaning that charge is neither introduced into the tissue nor removed from the tissue during the pause 43.

The individual pulses 40 of the pulse train 35 are in particular identical and are applied periodically with a frequency $f_{stim}$. The frequency $f_{stim}$ with which the individual pulses 40 are repeatedly applied within the pulse train 35 in particular amounts to at least 100 Hz; for example, the frequency $f_{stim}$ is in a range from 100 to 200 Hz. However, the frequency $f_{stim}$ may also assume even higher values. The period $T_{stim}=1/f_{stim}$ is illustrated in FIG. 2. The continuous application of a pulse train 35 with a frequency $f_{stim}$ of at least 100 Hz is referred to as continuous high-frequency stimulation.

During the time $t_{Pulse-to-Pulse}$ between two individual pulses 40 directly following one another within the pulse train 35, meaning between the end of the second pulse portion 42 of an individual pulse 40 and the beginning of the first pulse portion 41 of the directly following individual pulse 40, stimulation does not take place, meaning that the amplitude of the pulse train 35 is zero during the time $t_{Pulse-to-Pulse}$. It may be provided that the time $t_{Pulse-to-Pulse}$ between two individual pulses 40 in direct succession is longer than the duration $t_{Pause}$ of the pause 43 between the first and second pulse portion 41, 42 of an individual pulse 40. It is pointed out that the time $t_{Pulse-to-Pulse}$ is calculated as follows:

$$t_{Pulse-to-Pulse} = T_{stim} - t_1 - t_2 - t_{Pause} \qquad (1)$$

As explained further below, the pause 43 between the pulse portions 41, 42 of an individual pulse 40 significantly contributes to the stimulation success. According to one embodiment, the duration $t_{Pulse-to-Pulse}$ of the pause 43 is at least 1 ms. According to a further embodiment, the duration $t_{Pause}$ of the pause 43 is in a range from 1 ms to 6 ms. Furthermore, it may be provided that the duration $t_{Pause}$ of the pause 43 is adapted to the frequency $f_{stim}$ with which the individual pulses 40 are repeatedly applied within the pulse train 35. The greater the frequency $f_{stim}$, the shorter the period length $T_{stim}$. Under the secondary condition that $t_{Pause} < t_{Pulse-to-Pulse}$ applies, the maximum possible duration of the pause 43 becomes the smaller, the greater the frequency $f_{stim}$ becomes.

Furthermore, the control unit 10 may vary the duration $t_{Pause}$ of the pause 43 until the synchronization of the stimulated neurons is minimal or falls below a predetermined threshold.

The pulse train 35 with the periodically occurring individual pulses 40 is preferably applied continuously, meaning during a comparatively long time period. For example, the pulse train 35 is applied for longer than 30 minutes, or 1 hour, or 2 hours. During the application of the pulse train 35, no additional pauses are preferably observed aside from the pauses with lengths $t_{Pause}$ and $t_{Pulse-to-Pulse}$ described above.

The rectangular shape of the individual pulses 40 illustrated in FIG. 2, and in particular of the first and second pulse portions 41, 42, represents an ideal shape. Depending on the quality of the electronics generating the individual pulses 40, the ideal rectangular shape is deviated from.

The individual pulses 40 with the first and second pulse portions 41, 42, illustrated in FIG. 2, may also be referred to as individual stimuli 40 with first and second stimulus portions 41, 42 that are applied within a periodic stimulus sequence.

Instead of first and second pulse portions, first and second phases may also be referred to.

The amplitude of the pulse train 35 is modulated as described above with a modulation signal that the control unit 10 generates from the measurement signal 23. Since the measurement signal 23 reflects the pathologically, synchronous neuronal activity of the stimulated neurons, a feedback amplitude modulation is consequently performed, meaning an amplitude modulation with a feedback signal as modulation signal. The feedback modulation signal, called S(t) below, is additionally time-delayed and processed linearly or non-linearly in relation to the measurement signal 23 received by the measuring unit 13.

To generate the feedback modulation signal S(t), the measurement signal 23 is initially pre-processed, for example amplified and/or bandpass-filtered, wherein the physiologically relevant frequency range can pass through the bandpass filter. A pre-processed measurement signal 23 received at a point in time t is to be called x(t) below.

Moreover, I is the parameter of the stimulation intensity, and T indicates the time delay of the feedback modulation signal S(t) in relation to the measurement signal 23 or the pre-processed measurement signal x(t). To the linear delayed feedback modulation signal S(t), the following then applies:

$$S(\tau) = I(x(t-\tau) - x(t)) \qquad (2)$$

The amplitude of the pulse train 35 shown in FIG. 2 is modulated with the modulation signal S(t) in order to obtain the stimulation signal 22. Consequently, with H(t) for the signal of the pulse train 35, S(t)×H(t) results for the stimulation signal 22. The stimulation elements 12 administer the stimulation signal 22 to the neuronal tissue and stimulate the neurons with the pathologically synchronous neuronal activity in the target area 30.

The design of the amplitude modulation signal for a linear delayed feedback stimulation is described in M. G. Rosenblum, A. S. Pikovsky: Controlling synchronization in an ensemble of globally coupled oscillators. Phys. Rev. Lett. 92, 114102 (2004), and O. V. Popovych, C. Hauptmann, P. A. Tass: Control of neuronal synchrony by nonlinear delayed feedback. Biol. Cybern. 95, 69-85 (2006).

Furthermore, a non-linear delayed feedback modulation signal S(t) may be generated from the pre-processed measurement signal x(t) according to the following equation:

$$S(t) = I Z^2(t) Z^*(t-\tau), \qquad (3)$$

where the following applies to the signal Z(t):

$$Z(t) = x(t) + i y(t) \qquad (4)$$

Z*(t) indicates the complex conjugate of Z(t). The signal y(t), which represents the imaginary part of the signal Z(t), may be obtained from the signal x(t) via a Hilbert transformation. Alternatively, the signal y(t) may be generated from the signal x(t) by means of a time delay. For example, the signal x(t) may be shifted by one quarter of the mean period T of the pathologically synchronous, oscillatory neuronal activity of the stimulated neurons: y(t)=x(t−T/4). The mean period T of the pathologically synchronous, oscillatory neuronal activity of the stimulated neurons may be extracted from the measurement signal 23.

The stimulation signal 22 may be generated by multiplication of the signal H(t) of the pulse train 35 with the non-linear delayed feedback modulation signal S(t). Furthermore, instead of the complex modulation signal S(t), only the real part of this signal may be multiplied with the signal H(t) in order to obtain the stimulation signal 22. The following applies to the real part of the non-linear delayed feedback modulation signal S(t):

$$Re[S(t)] = I x(t-\tau)(x^2(t) - y^2(t)) + 2 I x(t) y(t) y(t-\tau) \qquad (5)$$

The design of the amplitude modulation signal for non-linear delayed feedback stimulation is described in O. V. Popovych, C. Hauptmann, P. A. Tass: Effective desynchronization by nonlinear delayed feedback. Phys. Rev. Lett. 94, 164102 (2005) and O. V. Popovych, C. Hauptmann, P. A. Tass: Control of neuronal synchrony by nonlinear delayed feedback. Biol. Cybern. 95, 69-85 (2006).

Figure 3:
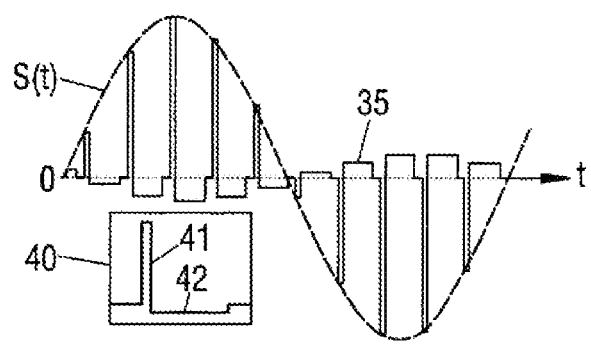
FIGS. 3 and 4 illustrate schematic illustrations of pulse trains whose amplitude was modulated with various modulation signals.
Figure 4:
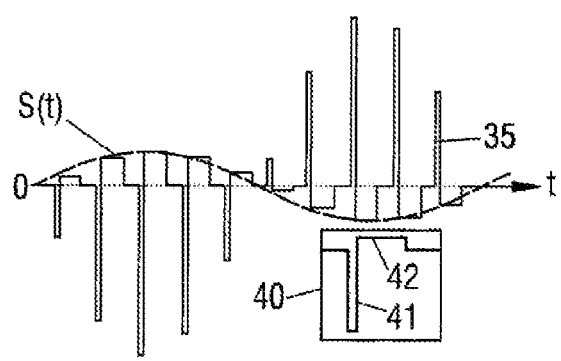

FIGS. 3 and 4 schematically show different electrical pulse trains whose amplitude was modulated with various feedback modulation signals S(t). FIGS. 3 and 4 respectively include a separate enlarged illustration of the respectively used individual pulse 40. It is to be noted that, in FIGS. 3 and 4, the pauses 43 between the first pulse portions 41 and the second pulse portions 42 of the individual pulses 40 are not shown in order to simplify the illustration.

In the pulse train 35 shown in FIG. 3, the first pulse portion 41 is respectively an anodic, positive phase, and the second pulse portion 42 is a cathodic, negative phase. In FIG. 4, the polarities of the two pulse portions 41, 42 are swapped in comparison to the pulse train 35 of FIG. 3, so that the first pulse portion 41 represents a cathodic phase and the second pulse portion 42 represents an anodic phase.

As can be learned from FIGS. 3 and 4, the individual pulses 40 are also dimensioned after the amplitude modulation with the feedback modulation signal S(t) such that precisely as much charge is introduced into the tissue by an individual pulse 40 during the actual stimulation phase as is removed from the tissue during the charge-balancing stimulation phase.

In the course of the invention, the following surprising observation was made: If the linear or non-linear delayed feedback stimulation signal S(t) is used for amplitude modulation of a periodic pulse train whose individual pulses do not have a pause between the first pulse portion and the second pulse portion, a sufficiently strong desynchronization is not achieved. However, if a pause 43 is inserted between the first pulse portion 41 and the second pulse portion 42 of the individual pulses 40 as in the pulse train 35 shown by way of example in FIG. 2 and the amplitude of the pulse train 35 is modulated with the linear or non-linear delayed feedback stimulation signal S(t), a fully pronounced desynchronization is achieved. A distinct improvement of the desynchronization is already achieved with a duration $t_{Pause}$ of the pause 43 of 1 ms. Better values for the duration $t_{Pause}$ of the pause 43 amount to 5 ms, for example.

It is likewise surprising that the continuous high-frequency stimulation with both linear and non-linear delayed feedback amplitude modulation and individual pulses with pauses between the pulse portions are comparable with regard to the dependency of the desynchronization effect on the time delay. This means that the non-linear variant is no longer markedly superior as is the case with conventional delayed feedback stimulation. The variant that can be realized more simply technically, i.e., the continuous high-frequency stimulation with linear delayed feedback amplitude modulation and individual pulses with pauses between the pulse portions, thus may be used. In the non-linear variant, the in particular undelayed signal component is likewise used in addition to the delayed, complexly conjugated signal component. In comparison thereto, it is simpler to merely chronologically delay the signal component, as in the linear variant.

According to one embodiment, the control unit 10 varies the time delay τ of the feedback modulation signal S(t) in relation to the measurement signal 23 or the pre-processed measurement signal x(t). The variation of the time delay τ may in particular be continued until the synchronization of the stimulated neurons is minimal or falls below a predetermined threshold.

Figure 11:
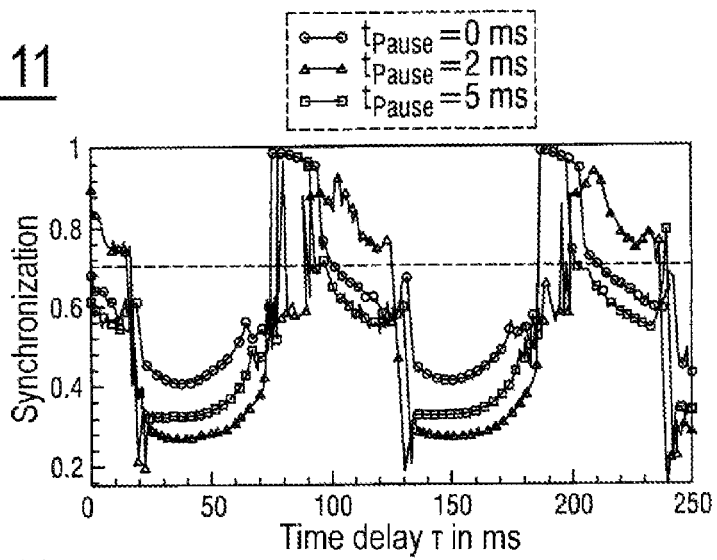
Figure 14:
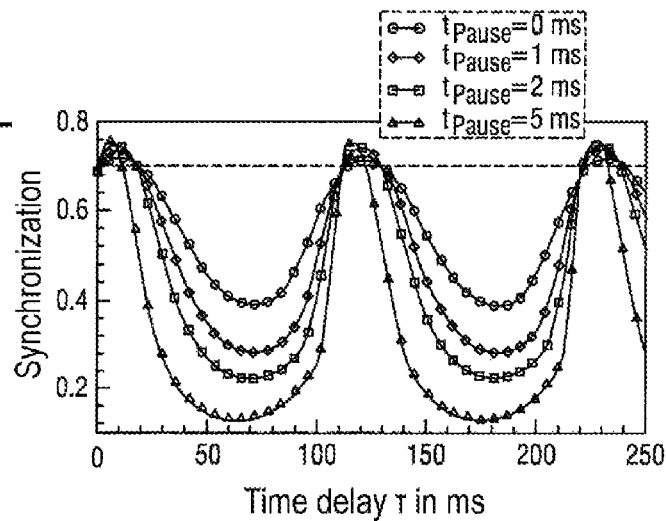
FIGS. 14 through 16 illustrates diagrams with stimulation results for a continuous high-frequency stimulation with a linear delayed feedback amplitude modulation, and individual pulses with and without pauses between successive pulse portions.

The optimal time delay τ may, for example, be in the range from 0.5 to 2.5 times or from 1.5 to 2.5 times the mean period of the pathological rhythmic activity of the affected neuron population. In particular, the time delay τ may be in a range from 5 ms to 2 s. The optimal value for the time delay τ may also strongly deviate therefrom—for example, caused by internal time delays in the neuron population, or in neuron populations interacting therewith. FIGS. 11 and 14, explained further below, show the dependency of the stimulation success on the time delay τ. The time delays belonging to regions of local minima of the synchronization typically repeat after a multiple of the mean period. This means that, in addition to an optimal time delay $\tau_{opt}$, the time delays $\tau_{opt}+T_{mean}$ or $\tau_{opt}+2\,T_{mean}$ are suitable for a pronounced desynchronization, wherein $T_{mean}$ denotes the mean period of the pathological rhythmic activity of the affected neuron population. The following calibration procedure may therefore be executed: The mean period $T_{mean}$ is determined, or a value known to the person skilled in the art is taken as a starting point. The latter is possible since the pathological oscillatory activity is located in typical frequency bands. The starting point is then a time delay $\tau=\alpha\cdot T_{mean}$, where $0<\alpha<0.5$, for example $\alpha=0.4$. The parameter α is then increased slowly until a pronounced desynchronization arises, meaning that the synchronization of the stimulated neurons reaches a local minimum or falls below a predetermined threshold. A further increase then leads to a decrease in the desynchronization. As soon as a value for a is reached that enables an optimal desynchronization, the intensity—meaning in particular the amplitude of the stimulation—may be slowly increased at the predetermined fixed value for α in order to be able to achieve an even more efficient desynchronization. For example, the increase in the intensity may be continued until the synchronization of the stimulated neurons reaches another local minimum or falls below another predetermined threshold. These control processes may be automated. However, the feedback of the patient and/or physician regarding the occurrence of possible side effects with increasing intensity should be taken into account so that the procedure may proceed safely and tolerably. Since the mean period $T_{mean}$ may vary over time, α should be regularly readjusted in order to enable an optimal desynchronization.

Figure 5:
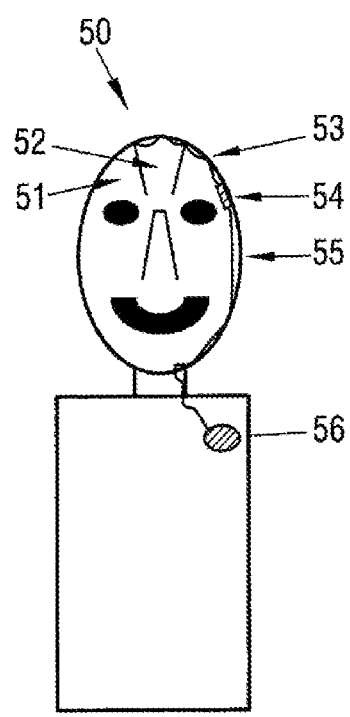
FIGS. 5 and 6 illustrate schematic illustrations of devices for desynchronization of neurons with pathologically synchronous and oscillatory neuronal activity by means of electrical stimulation signals, according to further embodiments.

FIG. 5 schematically shows a device 50 for invasive electrical stimulation of neurons with a pathologically synchronous and oscillatory neuronal activity according to an embodiment of the invention. The device 50 comprises two deep brain electrodes 51, 52 that are implanted into the brain of the patient and connected via cables 53 to a connector 54. The connector 54 in turn is connected via a cable 55 to a control unit 56. The control unit 56 generates the stimulation signals based on the measured feedback signals. The stimulation signals for the two brain electrodes 51, 52 may be generated separately. However, stimulation may also take place via one of the two brain electrodes 51, 52 and be measured via the other brain electrode. The device 50 may have the function of device 1 described above.

Figure 6:
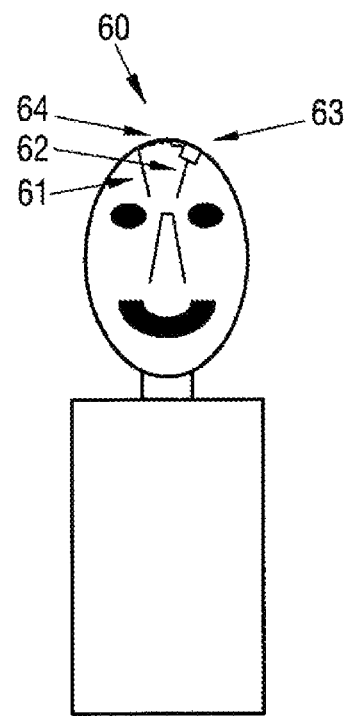

FIG. 6 schematically shows another device 60 for invasive electrical stimulation of neurons with a pathologically synchronous and oscillatory neuronal activity according to another embodiment of the invention. In the same manner as the device 50, device 60 comprises two implanted deep brain electrodes 61, 62. The device 60 also comprises a control unit 63 that is implanted in a bore hole and directly connected to the brain electrode 62. The brain electrode 61 is connected to the control unit 63 via a cable 64. The stimulation signals for the two brain electrodes 61, 62 may be generated separately. However, stimulation may also take place via one of the two brain electrodes 61, 62 and be measured via the other brain electrode. The device 60 may have the same functions as the device 1.

Figure 7:
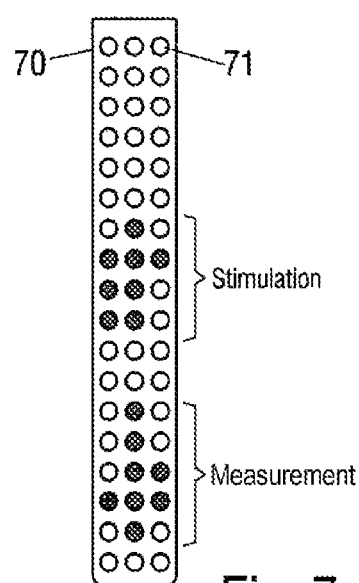
FIG. 7 illustrates a schematic illustration of a many-channel electrode.

FIG. 7 schematically shows a many-channel electrode 70, which serves as stimulation unit 11 and has a plurality of electrically conductive contacts or stimulation contact surfaces 71 which are arranged in an array and constitute the stimulation elements 12.

The contacts 71 may be controlled individually so that a desired electrical stimulation signal 22 may be applied via each contact 71. For example, the stimulation signal 22 may be spatially applied via multiple contacts 71 in a manner weighted according to anatomical and/or physiological boundary conditions. The contacts 71 may furthermore also be used to measure neuronal activity. Measurement or stimulation contacts 71 are respectively illustrated by dark circles in FIG. 7. As an example, measurement or stimulation takes place via different groups of contacts 71.

Figure 8:
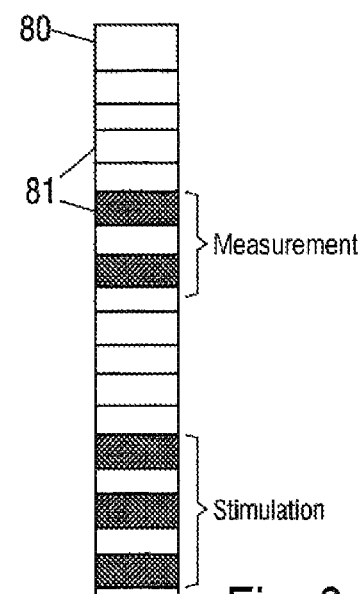
FIG. 8 illustrates a schematic illustration of a multi-channel electrode.

FIG. 8 schematically shows a multi-channel electrode 80, which serves as stimulation unit 11 and has a plurality of annular, electrically conductive contacts or stimulation contact surfaces 81 which constitute the stimulation elements 12. For example, measurement or stimulation takes place here via dark-marked contacts 81, whereas neither measurement nor stimulation takes place via white-marked contacts 81.

Figure 9:
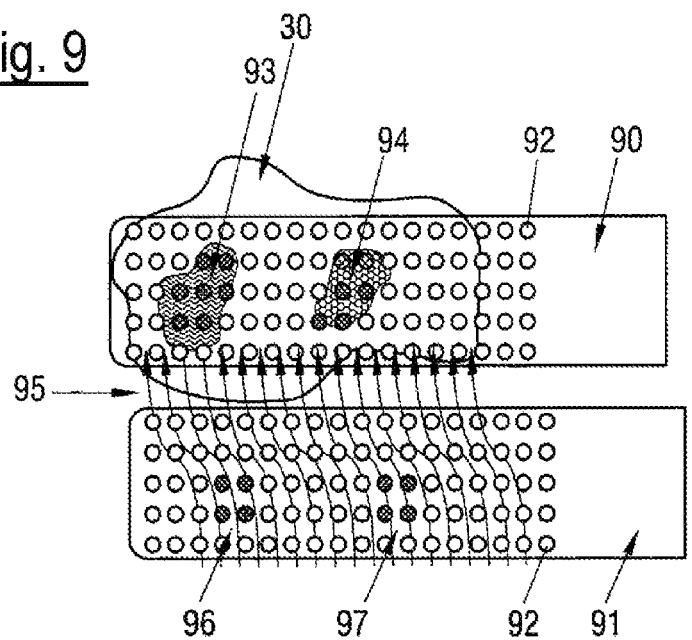
FIG. 9 illustrates a schematic illustration of a many-channel electrode for direct stimulation of a target area and/or derivation of measurement signals, and another many-channel electrode for indirect stimulation of the target area.

FIG. 9 schematically shows many-channel electrodes 90, 91, which respectively have a plurality of electrically conductive contacts 92 arranged in an array. Two neuron populations 93, 94 that interact with one another are stimulated in the target area 30 with the many-channel electrodes 90, 91. The many-channel electrode 90 is placed directly on the target area 30 for direct stimulation of the neuron populations 93, 94. The somata, axons, and dendrites of the neuron populations 93, 94 may thereby be stimulated directly. In the present example, the neuron populations 93, 94 are stimulated via the dark-filled contacts 92 associated with said neuron populations 93, 94. A group of contacts 92 is in this case associated with each of the neuron populations 93, 94. A measurement signal that reflects the neuronal activity of the stimulated neuron populations 93, 94 may also be derived via the many-channel electrode 90.

The many-channel electrode 91 is not placed directly on the target area 30; rather, afferent fibres 95 that lead to the neuron populations 93, 94 and/or originate therefrom are stimulated. In the exemplary embodiment shown in FIG. 9, groups 96, 97 are respectively formed from multiple contacts 92, and the neuron populations 93, 94 are indirectly stimulated with the groups 96, 97 via the afferent fibres 95. The contacts 92 of the groups 96, 97 are shown with a dark fill in FIG. 9.

Given a combined direct and indirect stimulation, one of the neuron populations 93, 94 may, for example, be stimulated exclusively directly, the other exclusively indirectly, with the continuous high-frequency stimulation described above with linear as well as non-linear delayed feedback amplitude modulation. In principle, a simultaneous and/or chronologically alternating combined direct and indirect stimulation of the same neuron population may also take place.

In direct and/or indirect electrical stimulation, the types of bipolar stimulation known to the person skilled in the art may be applied between pairs of contacts 92, and the types of unipolar stimulation known to the person skilled in the art may be applied between contacts 92 and a common ground. The measurement of the feedback signals takes place via monopolar and/or bipolar derivation in a manner known to the person skilled in the art.

Implantable stimulation units 11 for optical stimulation of neuronal tissue are known. For example, a light source, such as a laser, a laser diode, or an LED, may generate a light beam that is distributed with the aid of a light injection to the inputs of a fibre bundle consisting of multiple optical waveguides. A control unit 10 in this case specifies, for example, at which point in time an individual light pulse or a train of light pulses is injected into which fibres of the fibre bundle. The decoupling points of the individual fibres of the fibre bundle, i.e., the ends of the fibres, may be situated at various locations in the target area 30 in the brain and/or spinal cord of the patient. In this case, the light stimulates different sites of the target area 30 in a chronological sequence provided by the control unit 10. However, other implantable stimulation units 11 that are suitable for direct optical stimulation of neuronal tissue may also be used. In the event of optical stimulation signals 22, the luminous intensity of a pulse train is amplitude-modulated with the feedback modulation signal S(t).

In FIGS. 10 through 16, the effects that can be achieved with the invention described herein are illustrated using simulation results.

Figure 10:
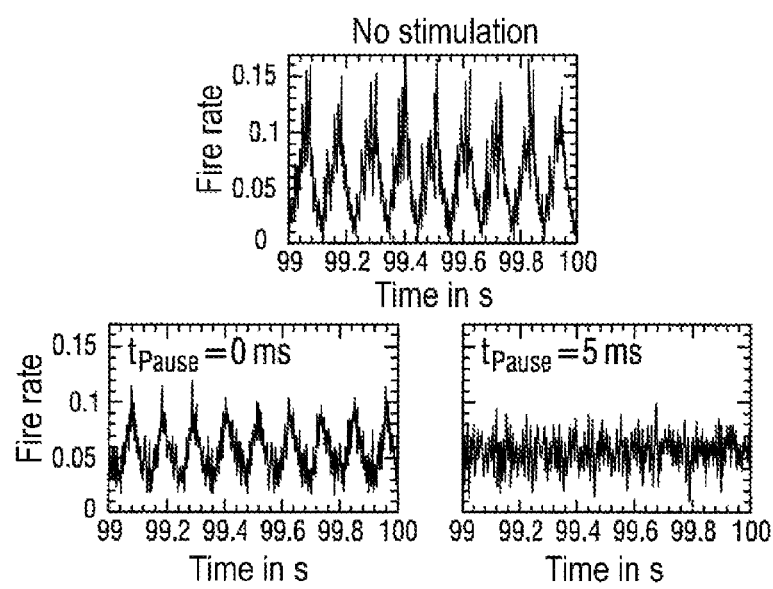
FIGS. 10 through 13 illustrate diagrams with stimulation results for a continuous high-frequency stimulation with a non-linear delayed feedback amplitude modulation, and individual pulses with and without pauses between successive pulse portions.

The desynchronization effect that is produced by the invention is shown in FIG. 10 with reference to the fire rate of a neuron population. The fire rate indicates the relative number of neurons that fire at a respective point in time. In the illustrations of FIG. 10, the fire rate of the neurons is plotted against time. The rhythmic firing of the neurons of the pathologically synchronously active neuron populations before stimulation is shown in the upper illustration of FIG. 10. The synchronization of the neurons is significantly reduced by means of a continuous high-frequency stimulation with non-linear delayed feedback amplitude modulation, as the two lower illustrations of FIG. 10 show. A stimulation with individual pulses that have a pause $t_{Pause}$ of 5 ms between the first pulse portion and second pulse portion is in this case markedly superior to a stimulation with individual pulses whose first and second pulse portions directly follow one another, i.e. for which $t_{Pause}=0$.

Illustrated in FIG. 11 is the degree of synchronization of a neuron population with a pathologically synchronous and oscillatory neuronal activity in dependence on the time delay τ for a continuous high-frequency stimulation with a non-linear delayed feedback amplitude modulation. The time delay τ determines by what time period the feedback modulation signal S(t) is delayed in relation to the measurement signal x(t). The simulation was performed for individual pulses with pauses $t_{Pause}$ of 0.2 or 5 ms and fixed stimulation intensity I. The horizontal dashed line in FIG. 11 indicates the degree of synchronization of the neuron population before stimulation. It may be learned from FIG. 11 that, for specific sub-ranges of the time delay r, a markedly more effective desynchronization of the neuron population can be achieved if a pause is observed between the pulse portions of the individual pulses.

Figure 12:
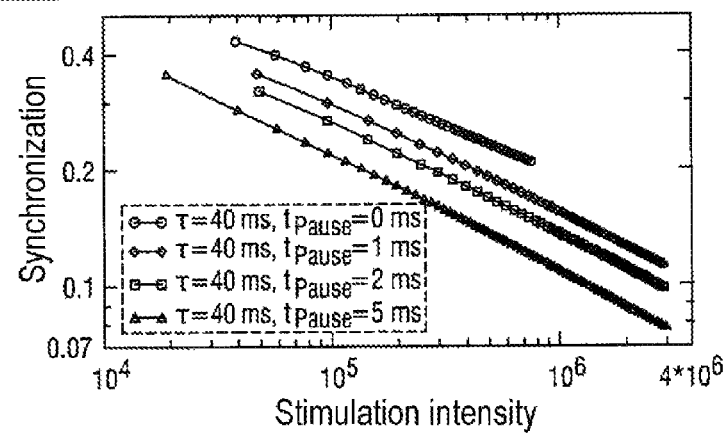

The desynchronization effect achieved by the pause between the pulse portions of the individual pulses is moreover intensified given an increasing stimulation intensity I. This property is shown in FIG. 12, in which the degree of synchronization of the stimulated neuron population is plotted against the stimulation intensity I for a fixed time delay τ of 40 ms and values for the pause $t_{Pause}$ of 0, 1, 2, or 5 ms. In the present example, a continuous high-frequency stimulation with a non-linear delayed feedback amplitude modulation without pause between the individual pulses desynchronizes the neuron population only to a certain degree. The same stimulation with a pause between the individual pulses yields significantly better results.

A higher stimulation intensity I furthermore leads to a strong desynchronization of the neuron population.

Figure 13:
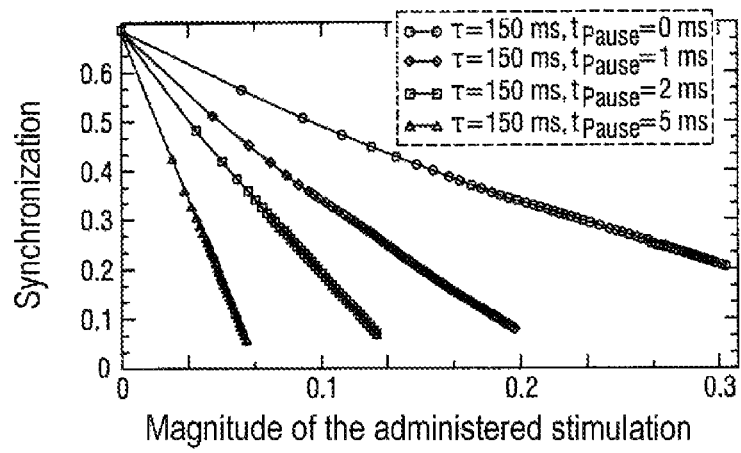

The effectiveness of the stimulation described herein is shown in FIG. 13, in which the degree of the synchronization is plotted against the magnitude of the administered stimulation. The magnitude of the administered stimulation is provided by the amplitude of the feedback modulation signal S(t), as shown by way of example in FIGS. 3 and 4. The values illustrated in FIG. 13 are based upon a simulation of a continuous high-frequency stimulation with a non-linear delayed feedback amplitude modulation with a fixed time delay τ of 150 ms and pauses $t_{Pause}$ of 0, 1, 2, or 5 ms. FIG. 13 shows that a stimulation with a longer pause $t_{Pause}$ requires a smaller magnitude of the administered stimulation in order to achieve the same desynchronization effect as a stimulation with a shorter pause $t_{Pause}$.

Figure 15:
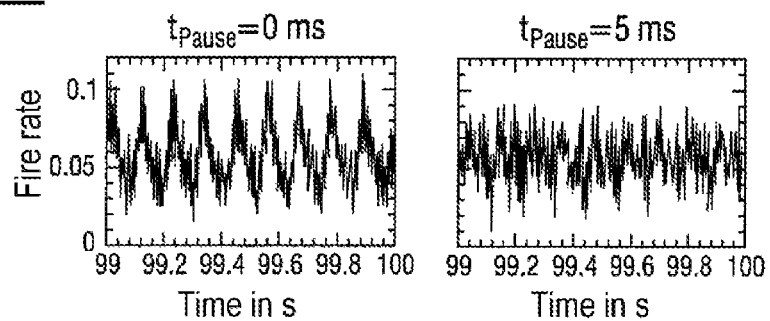
Figure 16:
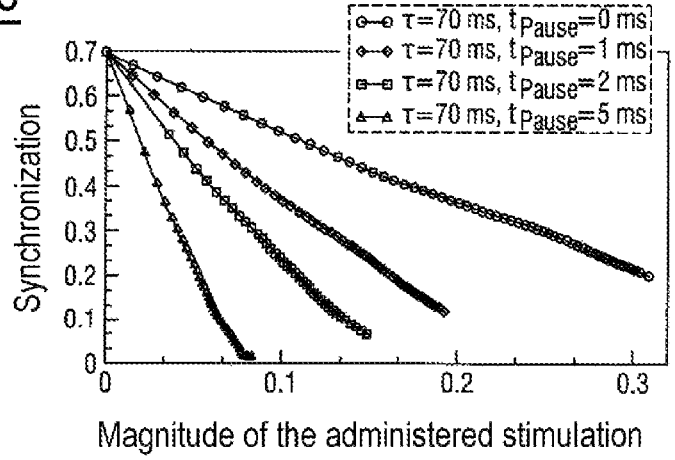

Whereas the simulation results shown in FIGS. 10 through 13 were based on a continuous high-frequency stimulation with a non-linear delayed feedback amplitude modulation, FIGS. 14 through 16 show simulation results of a continuous high-frequency stimulation with a linear delayed feedback amplitude modulation.

Analogously to FIG. 11, FIG. 14 shows the degree of synchronization of a neuron population with a pathologically synchronous and oscillatory neuronal activity in dependence on the time delay τ for a continuous high-frequency stimulation with a linear delayed feedback amplitude modulation. The simulation was performed for individual pulses with pauses $t_{Pause}$ of 0, 1, 2, or 5 ms and fixed stimulation intensity I. The horizontal dashed line in FIG. 14 indicates the degree of synchronization of the neuron population before stimulation. A comparison with the results illustrated in FIG. 11 shows that the linear delayed feedback amplitude modulation is superior to the non-linear delayed feedback amplitude modulation for specific values of the time delay τ given otherwise identical parameters.

In FIG. 15, the fire rate of the neurons is plotted against time, which fire rate is produced by a continuous high-frequency stimulation with a linear delayed feedback amplitude modulation and individual pulses without or with pause $t_{Pause}$ between the pulse portions. Just as with the non-linear delayed feedback amplitude modulation, the stimulation with individual pulses that have a pause $t_2$ of 5 ms between the first and second pulse portion is in this case markedly superior to a stimulation with individual pulses whose first and second pulse portions directly follow one another.

In the illustration of FIG. 16, the degree of the synchronization is plotted against the magnitude of the administered stimulation that can be achieved with a continuous high-frequency stimulation with a linear delayed feedback amplitude modulation with a fixed time delay τ of 70 ms and pauses $t_{Pause}$ of 0, 1, 2, or 5 ms. Here as well, a stimulation with a longer pause $t_{Pause}$ leads to the same desynchronization effect as a stimulation with a shorter pause $t_{Pause}$ but a higher magnitude of the administered stimulation.

The invention claimed is:

1. A device for stimulating neurons, comprising:
   a stimulation unit configured to be implanted into a body of a patient and having at least one stimulation element configured to apply a stimulation signal to tissue of the patient to stimulate neurons in at least one of the brain and the spinal cord of the patient;
   a measuring unit configured to receive a measurement signal that reflects a neuronal activity of the stimulated neurons; and
   a control unit coupled to stimulation unit and the measuring unit, the control unit configured to:
   generate a modulation signal from the measurement signal,
   modulate an amplitude of a pulse train comprising a plurality of individual pulses with the modulation signal, and
   control the stimulation unit such that the at least one stimulation element applies the amplitude-modulated pulse train as the stimulation signal to stimulate the neurons,
   wherein the individual pulses respectively have a first pulse portion and a second pulse portion following the first pulse portion,
   wherein one of the first pulse portion and the second pulse portion introduces a charge into the tissue, and the other of the first and second pulse portions removes the charge from the tissue,
   wherein a respective pause is provided between the first pulse portion and the second pulse portion of the individual pulses,
   wherein the stimulation signal is configured to desynchronize a pathologically synchronous and oscillatory activity of the stimulated neurons upon administration to the patient,
   wherein the measurement signal reflects the pathologically synchronous and oscillatory activity of the stimulated neurons, and
   wherein the control unit is configured to vary the pause between the first pulse portion and the second pulse portion until the synchronization of the stimulated neurons is minimized or falls below a predetermined threshold.

2. The device according to claim 1, wherein the individual pulses within the pulse train are repeated one of continuously or periodically.

3. The device according to claim 1, wherein the individual pulses within the pulse train are repeated periodically with a frequency of at least 100 Hz.

4. The device according to claim 1, wherein the pause between the first pulse portion and the second pulse portion is at least 1 millisecond.

5. The device according to claim 1, wherein the control unit is further configured to pre-process the measurement signal by at least one of amplification and bandpass filtering and to generate the modulation signal from the pre-processed measurement signal.

6. The device according to claim 1, wherein the control unit is further configured to process the measurement signal with a time delay and linearly in order to generate the modulation signal.

7. The device according to claim 1, wherein the control unit is further configured to process the measurement signal with a time delay and non-linearly in order to generate the modulation signal.

8. The device according to claim 1, wherein the control unit is further configured to vary a time delay of the measurement signal to generate the modulation signal until the synchronization of the stimulated neurons reaches a first minimum or falls below a first predetermined threshold.

9. The device according to claim 8, wherein the control unit is further configured to increase an intensity of the stimulation signal after the time delay is varied until the synchronization of the stimulated neurons reaches a second minimum or falls below a second predetermined threshold.

10. The device according to claim 1, wherein the pulse train is one of an electrical pulse train and an optical pulse train.

11. The device according to claim 1, wherein the first and second pulse portions are dimensioned such that the one of the pulse portions introduces a same amount of charge into the tissue as the other of the pulse portions removes from the tissue.

12. The device according to claim 1, wherein the pause between the first pulse portion and the second pulse portion of the individual pulses is smaller than the pause between the second pulse portion of an individual pulse and the first pulse portion of a directly following individual pulse in the pulse train.

13. A method for stimulating neurons, the method comprising:
  applying, by at least one stimulation element of a stimulation unit configured to be implanted into a body of a patient, a stimulation signal to tissue of the patient to stimulate neurons in at least one of the brain and the spinal cord of the patient, wherein the stimulation signal is configured to desynchronize a pathologically synchronous and oscillatory activity of the stimulated neurons upon administration to the patient,
  receiving, by a measuring unit, a measurement signal that reflects a neuronal activity of the stimulated neurons, wherein the measurement signal reflects the pathologically synchronous and oscillatory activity of the stimulated neurons;
  generating, by a control unit, a modulation signal from the measurement signal;
  modulating, by the control unit, an amplitude of a pulse train comprising a plurality of individual pulses with the modulation signal, wherein the individual pulses respectively have a first pulse portion and a second pulse portion following the first pulse portion and one of the first pulse portion and the second pulse portion introduces a charge into the tissue and the other of the first and second pulse portions removes the charge from the tissue;
  controlling, by the control unit, the stimulation unit such that the at least one stimulation element applies the amplitude-modulated pulse train as the stimulation signal to stimulate the neurons;
  providing, by the control unit, a respective pause between the first pulse portion and the second pulse portion of the individual pulses; and
  varying, by the control unit, the pause between the first pulse portion and the second pulse portion until the synchronization of the stimulated neurons is minimized or falls below a predetermined threshold.

14. The method according to claim 13, further comprising repeating the individual pulses within the pulse train either continuously or periodically.

15. The method according to claim 13, further comprising varying, by the control unit, a time delay of the measurement signal to generate the modulation signal until the synchronization of the stimulated neurons reaches a first minimum or falls below a first predetermined threshold.

16. The method according to claim 13, further comprising increasing, by the control unit, an intensity of the stimulation signal after the time delay is varied until the synchronization of the stimulated neurons reaches a second minimum or falls below a second predetermined threshold.

17. The method according to claim 13, wherein the pulse train is one of an electrical pulse train and an optical pulse train.

18. The method according to claim 13, further comprising dimensioning the first and second pulse portions such that the one of the pulse portions introduces a same amount of charge into the tissue as the other of the pulse portions removes from the tissue.

19. The method according to claim 13, wherein the pause between the first pulse portion and the second pulse portion of the individual pulses is smaller than the pause between the second pulse portion of an individual pulse and the first pulse portion of a directly following individual pulse in the pulse train.

20. A tangible, non-transitory computer-readable medium having instructions thereon, which upon execution by one or more processors, facilitate performance of the following steps:
  apply, by at least one stimulation element of a stimulation unit configured to be implanted into a body of a patient, a stimulation signal to tissue of the patient to stimulate neurons in at least one of the brain and the spinal cord of the patient, wherein the stimulation signal is configured to desynchronize a pathologically synchronous and oscillatory activity of the stimulated neurons upon administration to the patient,
  receive, by a measuring unit, a measurement signal that reflects a neuronal activity of the stimulated neurons, wherein the measurement signal reflects the pathologically synchronous and oscillatory activity of the stimulated neurons;
  generate, by a control unit, a modulation signal from the measurement signal;
  modulate, by the control unit, an amplitude of a pulse train comprising a plurality of individual pulses with the modulation signal, wherein the individual pulses respectively have a first pulse portion and a second pulse portion following the first pulse portion and one of the first pulse portion and the second pulse portion introduces a charge into the tissue_and the other of the first and second pulse portions removes the charge from the tissue;
  control, by the control unit, the stimulation unit such that the at least one stimulation element applies the amplitude-modulated pulse train as the stimulation signal to stimulate the neurons;
  provide, by the control unit, a respective pause between the first pulse portion and the second pulse portion of the individual pulses; and
  vary, by the control unit, the pause between the first pulse portion and the second pulse portion until the synchronization of the stimulated neurons is minimized or falls below a predetermined threshold.

* * * * *